United States Patent [19]

Iimura et al.

[11] Patent Number: 4,874,856
[45] Date of Patent: * Oct. 17, 1989

[54] 3-(SUBSTITUTED)PROPENYL-7-(AMINO-THIAZOLYLACETAMIDO) CEPH-3-EM-4-CARBOXYLIC ACIDS AND ESTERS THEREOF

[75] Inventors: Seiji Iimura; Yoshio Abe, both of Tokyo; Jun Okumura, Yokohama; Takayuki Naito, Kawasaki; Hajime Kamachi, Chiba, all of Japan

[73] Assignee: Bristol-Myers Company, New York, N.Y.

[*] Notice: The portion of the term of this patent subsequent to Nov. 24, 2004 has been disclaimed.

[21] Appl. No.: 86,138

[22] Filed: Aug. 17, 1987

Related U.S. Application Data

[63] Continuation-in-part of Ser. No. 882,110, Jul. 3, 1986, abandoned, which is a continuation-in-part of Ser. No. 748,359, Jun. 24, 1985, Pat. No. 4,708,955.

[51] Int. Cl.$^4$ ........................................... C07D 501/46
[52] U.S. Cl. .................................................. 540/222
[58] Field of Search ....................................... 540/222

[56] References Cited

U.S. PATENT DOCUMENTS

| | | | |
|---|---|---|---|
| 3,971,778 | 11/1972 | Cook et al. | 540/227 |
| 4,065,620 | 6/1971 | Webber | 540/215 |
| 4,307,116 | 5/1980 | Farge et al. | 514/206 |
| 4,307,230 | 5/1980 | Farge et al. | 540/217 |
| 4,307,233 | 5/1980 | Farge et al. | 540/215 |
| 4,396,618 | 11/1979 | Heymes et al. | 514/207 |
| 4,515,788 | 5/1985 | Takaya | 540/222 |
| 4,559,334 | 10/1983 | Takaya et al. | 514/202 |
| 4,585,860 | 5/1983 | Takaya et al. | 514/202 |
| 4,654,331 | 8/1984 | Christensen | 514/120 |
| 4,708,955 | 11/1987 | Iimura | 514/202 |

FOREIGN PATENT DOCUMENTS

| | | |
|---|---|---|
| 30630 | 6/1981 | European Pat. Off. |
| 53074 | 6/1982 | European Pat. Off. |
| 53537 | 6/1982 | European Pat. Off. |
| 53538 | 6/1982 | European Pat. Off. |
| 88385 | 9/1983 | European Pat. Off. ............ 540/222 |
| 1399086 | 6/1975 | United Kingdom . |
| 2178038 | 2/1987 | United Kingdom ................ 540/222 |

OTHER PUBLICATIONS

Kamachi, H. et al, Journal of Antibiotics, vol. 41, No. 11, pp. 1602–1616 (1988).
Derwent Publications Abstract No. 83-835155/49 referring to Japanese 8135894-A (Fujisawa), Aug. '83.
Dunn, Journal of Antimicrobial Chemotherapy (1982), II, Suppl. C, 1–10.

Primary Examiner—Donald G. Daus
Attorney, Agent, or Firm—Robert E. Carnahan

[57] ABSTRACT

This invention provides novel cephalosporanic acids and esters thereof having the general formula

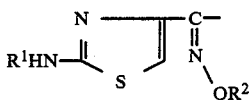

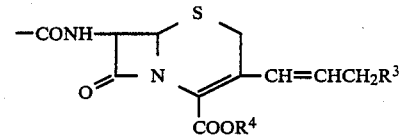

wherein $R^2$ is hydrogen, or lower acyl, $R^3$ is hydrogen, or lower alkanoyloxy, and
$R^4$ is hydrogen, 5-methyl-2-oxo-1,3-dioxolen-4-ylmethyl, 1-(ethoxycarbonyloxy)ethyl, 1-(pivaloyloxy)ethyl, 1-(cyclohexylacetoxy)ethyl, or 1-(cyclohexyloxycarbonyloxy) ethyl. These compounds, especially esters, are useful as broad spectrum antibiotics in the treatment and prevention of infectious diseases of mammals, and for other purposes known in the art. The acids ($R^4$ is hydrogen) are useful as intermediates for making the esters.

13 Claims, No Drawings

3-(SUBSTITUTED)PROPENYL-7-(AMINO-THIAZOLYLACETAMIDO) CEPH-3-EM-4-CARBOXYLIC ACIDS AND ESTERS THEREOF

REFERENCE TO RELATED APPLICATION

This application is a continuation-in-part of Ser. No. 882,110 filed July 3, 1986 and now abandoned, which is in turn a continuation-in-part of co-pending application Ser. No. 748,359 filed June 24, 1985, now U.S. Pat. No. 4,708,955 patented Nov. 24, 1987. The specifications of those applications are incorporated herein by reference.

BACKGROUND AND PRIOR ART (A) Published European patent application No. 30,630 discloses a vast number of 7-acylamino-3-vinyl-cephalosporanic acid derivatives including, inter alia, those of the formula

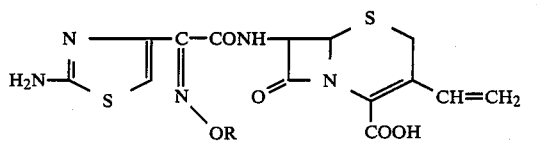

wherein R inter alia may be (lower) alkyl, (lower) alkenyl, (lower) alkynyl or carboxy (lower) alkyl. The compounds are prepared, inter alia by reaction of the corresponding 3-halomethyl compound with a triarylphosphine, followed by treatment with a base and reaction with formaldehyde. In each case, the final 3-substituent is the vinyl group. There is no disclosure or suggestion of a propenyl or a substituted propenyl moiety for the 3-substituent. There is also no disclosure or suggestion of an ester as pro-drug for oral use referring to the 4-carboxylic acid moiety. That compound wherein R is —CH$_2$CO$_2$H has been referred to in the literature as FK-027 and as cefixime. Related compounds in which R is —H or —CH$_3$ are disclosed by Takaya, et al., in U.S. Pat. Nos. 4,559,334 and 4,585,860 patented Dec. 17, 1985 and Apr. 29, 1986 respectively.

(B) U.K. Patent Specification No. 1,399,086 contains a generic disclosure encompassing a vast number of cephalosporins of the formula

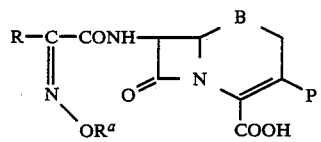

wherein R is hydrogen or an organic group, R$^a$ is an etherifying monovalent organic group linked to the oxygen through a carbon atom, B is S or S=O, and P is an organic group. In one embodiment, P may be inter alia a vinyl group of the formula

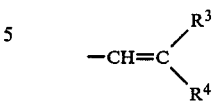

in which R$^3$ and R$^4$ independently may be hydrogen, nitrile, (lower)alkoxycarbonyl, or substituted or unsubstituted aliphatic, cycloaliphatic, araliphatic or aromatic. However, the 2-aminothiazol-4-yl group is not identified as a possible R substituent and there is no disclosure or suggestion about an ester as pro-drug for oral use concerning the 4-carboxylic acid thereof. U.S. Pat. No. 3,971,778 and its divisionals Nos. 4,024,133, 4,024,137, 4,064,346, 4,033,950, 4,079,178, 4,091,209, 4,092,477, and 4,093,803 have similar disclosures.

(C) U.S. Pat. No. 4,307,233 discloses, inter alia, 3-vinyl cephalosporin derivatives of the formula

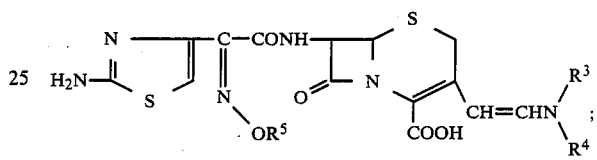

in which R$^5$ inter alia may be alkyl, vinyl, cyanomethyl or a protective group such as 2-methoxyprop-2-yl, and R$^3$ and R$^4$ are alkyl groups (optionally substituted by hydroxy, alkoxy, amino, alkylamino or dialkylamino) or phenyl groups, or R$^3$ and R$^4$, taken together with the nitrogen to which they are attached, may form a saturated heterocyclic ring of 5 or 6 members, optionally containing another heteroatom selected from N, O and S, and optionally substituted by an alkyl group. The compounds are useful as intermediates in the preparation of 3-thiovinyl cephalosporin derivatives. There is no disclosure or suggestion of a substituted or an unsubstituted propenyl moiety for the 3-substituent and also no disclosure or suggestion concerning a pro-drug ester for oral use for the 4-carboxylic acid. Published United Kingdom patent application No. 2,051,062 is concordant thereto and has a similar disclosure.

(D) Published European patent application No. 53,537 discloses, inter alia, 3-vinylcephalosporin derivatives of the formula

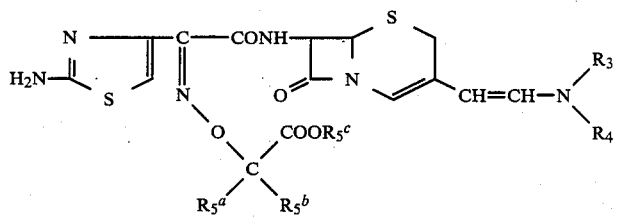

in which R$_5{}^a$ and R$_5{}^b$ are the same or different and are hydrogen or alkyl, or taken together, form an alkylene group containing 2 or 3 carbon atoms, R$_5{}^c$ is an acid protecting group, R$_2$ is an acid protecting group such as an ester, R$_3$ and R$_4$ are the same or different and are hydrogen, alkyl (optionally substituted by hydroxy, alkoxy, amino, alkylamino or dialkylamino) or phenyl groups, or R$_3$ and R$_4$, taken together with the nitrogen to which they are attached, may form a saturated heterocyclic ring of 5 or 6 members, optionally containing another heteroatom selected from N, O and S, and optionally substituted by an alkyl group. The compounds are useful as intermediates in the preparation of 3-thiovinyl cephalosporin derivatives. There is no disclosure or suggestion of a substituted or an unsubstituted propenyl group for the 3-substituent and an ester of the 4-carboxylic acid for oral use.

(E) U.S. Pat. No. 4,307,116 discloses 3-thiovinylcephalosporins of the formula

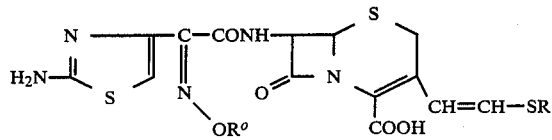

in which $R^o$ is hydrogen, alkyl, vinyl or cyanomethyl, and R inter alia may be one of a vast number of heterocyclic rings. There is no disclosure or suggestion of a substituted or an unsubstituted propenyl moiety for the 3-substituent and also there is no disclosure or suggestion of an ester thereof for oral use.

(F) Published European patent application No. 53,074 generically discloses a vast number of 3-vinylcephalosporin derivatives of the formula

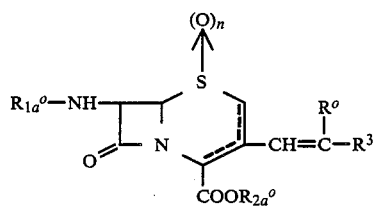

wherein $R_{1a}^o$ (in one of several embodiments) may be

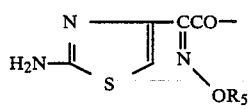

in which $R^5$ inter alia may be hydrogen, alkyl, vinyl, cyanomethyl, an oxime-protecting group such as trityl, etc., or a group of the formula

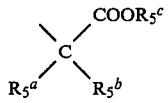

in which $R_5^a$ and $R_5^b$ are the same or different, and may be hydrogen, alkyl or, taken together, an alkylene radical of 2 or 3 carbon atoms, and $R_5^c$ is hydrogen or an acid-protecting radical; $R_{2a}^o$ is hydrogen or an acid-protecting radical such as methoxymethyl;

$R^o$ (in one of several embodiments) may be a methyl group substituted by a 5- or 6-membered aromatic heterocyclic ring containing a single heteroatom, such as 2- or 3-pyridyl, 2- or 3-thienyl or 2- or 3-furyl; and $R_3$ is a group of the formula $$R_4SO_2O—$$

in which $R_4$ may be alkyl, trihalomethyl or optionally substituted phenyl. These compounds are stated to be intermediates in the preparation of compounds in which the 3-substituent is a group of the formula

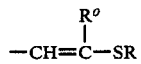

which are stated to have antibacterial activity. Although this patent includes the possibility of $R^o$ being a methyl group substituted by an N-containing heterocyclic ring, in both the intermediates and final product (thus giving a heterocyclic-substituted propenyl moiety), the reference exemplifies $R^o$ in the intermediates and final product only as methyl and further in both the intermediates and final product, the propenyl group must contain a second substituent ($—O_3SR^4$ or $—SR$ respectively). There is no disclosure or suggestion of an ester thereof for oral use.

(G) Published European patent application No. 53,538 discloses, inter alia, 3-vinylcephalosporin intermediates of the formula

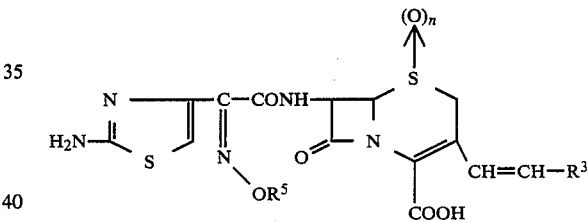

in which n is 0 or 1, $R^5$ is hydrogen, alkyl, vinyl, cyanomethyl or an oxime-protecting group, and $R^3$ is halogen.

(H) B. G. Christensen in U.S. Pat. No. 4,654,331 patented Mar. 31, 1987 discloses various (5-R-2-oxo-1,3-dioxolen-4-yl) methyl esters of certain cephalosporin antibiotics, and other physiological useful acids.

SUMMARY OF THE INVENTION

This application relates to novel cephalosporin derivatives which are potent antibacterial agents and more of which may be used orally. More particularly, it relates to compounds of the formula

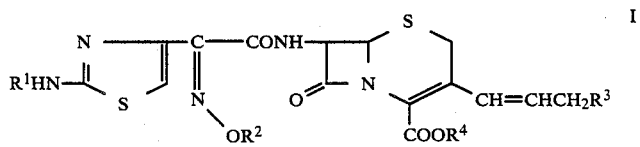

I wherein $R^1$ is hydrogen or a conventional amino-protecting group $R^2$ is hydrogen, or acyl having 2 to 4 carbon atoms, $R^3$ is hydrogen or lower alkanoyloxy having 2 to 3 carbon atoms, and when $R^2$ and $R^3$ are each hydrogen, $R^4$ is also hydrogen, and $R^4$ is hydrogen or a physiologically hydrolyzable ester group such as 5-methyl-2-oxo-1,3-dioxolen-4-ylmethyl, 1-(ethoxycarbonyloxy)ethyl, 1-(pivaloyloxy)ethyl, 1-(cyclohexylacetoxy)ethyl, or 1-(cyclohexyloxycarbonyloxy)ethyl.

Also included within the scope of the invention are the pharmaceutically acceptable acid addition salts, the metal salts (when $R^4$ is H) and the solvates (including hydrates) of the compounds of Formula I, which may exist in various tautomeric forms which are also included, e.g. the 2-iminothiazolin-4-yl form of the 2-aminothiazol-4-yl moiety.

As shown in the structural formula, the compounds of Formula I have the "syn" or "Z" configuration with respect to the $OR^2$ group. Because the compounds are geometric isomers, some of the "anti" isomer may also be present. This invention comprises compounds of Formula I containing at least 90% of the "syn" isomer. Preferably, the compounds of Formula I are "syn" which are essentially free of the corresponding "anti" isomers.

In addition to geometric isomers possible with respect to the $OR^2$ group, the compounds of Formula I also form geometric (cis and trans, or Z and E) isomers about the double bond of the propenyl group at the 3-position. Both the cis ("Z") and trans ("E") isomers of these compounds are specifically included within the scope of this invention.

The pharmaceutically acceptable acid addition salts of Formula I are those in which anion does not contribute significantly to the toxicity of the salt and are compatible with the customary pharmaceutical vehicles and adapted for oral or parenteral administration. The pharmaceutically acceptable acid addition salts include the salts of Formula I with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, p-toluenesulfonic acid and other acids known and used in the penicillin and cephalosporin arts. Preparation of these salts is carried out by conventional techniques involing reaction of Formula I with the acid in a substantially equivalent amount.

Those substances of Formula I wherein $R^4$ is hydrogen also form pharmaceutically acceptable metal and amine salts in which the cation does not contribute significantly to the toxicity or biological activity of the salt. These salts are also part of the present invention. Suitable metal salts include the sodium, potassium, barium, zinc and aluminum salts. The sodium or potassium salts are preferred. Amine salts prepared from amines used, for instance, with benzyl penicillin which are capable of forming stable salts with the acidic carboxyl group include trialkylamines such as triethylamine, procaine, dibenzylamine, N-benzyl-$\beta$-phenethylamine, 1-ephenamine, N,N'-dibenzylethylenediamine, dehydroabiethylamine, N-ethylpiperidine, benzylamine and dicyclohexylamine.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Suitable esters are the acetoxymethyl, pivaloyloxymethyl, 1-acetoxyethyl, 1-pivaloyloxyethyl, 3-phthalidyl, p-glycyloxybenzoyloxymethyl, 5-methyl-1,3-dioxacyclopent-4-en-2-on-4-ylmethyl, 1-(cyclohexylacetoxy)ethyl, 1-(cyclohexyloxycarbonyloxy)ethyl, and others known in the penicillin and cephalosporin art. The most preferred esters are 1-acetoxyethyl, pivaloyloxymethyl, and 1-(cyclohexyloxycarbonyloxy)ethyl.

The compounds of Formula I may be formulated for oral or parenteral use in a conventional manner using known pharmaceutical carriers and excipients, and they may be presented in unit dosage form or in multiple-dose containers. The compositions may be in the form of tablets, capsules, solutions, suspensions or emulsions. These compounds may also be formulated as suppositories utilizing conventional suppository bases such as cocoa butter or other fatty materials. The compounds may, if desired, be administered in combination with other antibiotics including cephalosporins, penicillins and aminoglycosides.

When provided in unit dosage forms, the compositions will preferably contain from about 50 to about 1500 mg of the active ingredient of Formula I. The dosage of the compounds of Formula I is dependent on such factors as the weight and age of the patient, as well as the particular nature and severity of the disease, and within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient.

In the compounds of Formula I, hydrogen is particularly preferred for $R^1$, hydrogen, or acetyl for $R^2$ and pivaloyloxymethyl, 1-acetoxyethyl, or 1-(cyclohexyloxycarbonyloxy)ethyl for $R^4$. Some compounds of this invention and of the parent applications, Ser. Nos. 748,359 and 882,110 are listed below. The experimental details for preparation and characterization of some compounds of this invention follow. Those which are not shown by specific example are readily prepared by analagous procedures. Like Compound Numbers and Example Numbers herein and in the parent applications refer to the same compounds in each.

Amino-protecting groups $R^1$ are well known in the art and include the trityl and acyl groups such as chloroacetyl, formyl, trichloroethoxycarbonyl, tert.-butoxycarbonyl, carbobenzyloxy, etc. Amino protecting groups which are readily hydrolyzed under acid conditions are preferred.

(29) 7$\beta$-[(Z)-2-(2-aminothiazol-4-yl)-2-(hydroxyimino)acetamido]-3-[(Z)-prop-1-en-1-yl]-3-cephem-4-carboxylic acid,

(30) 1-acetoxyethyl 7$\beta$-[(Z)-2-(2-aminothiazol-4-yl)-2-(hydroxyimino)acetamido]-3-[(Z)-prop-1-en-1-yl]-3-cephem-4-carboxylate,

(31) pivaloyloxymethyl 7$\beta$-[(Z)-2-(2-aminothiazol-4-yl)-2-(hydroxyimino)acetamido]-3-[(Z)-prop-1-en-1-yl]-3-cephem-4-carboxylate,

(32) acetoxymethyl 7$\beta$-[(Z)-2-(2-aminothiazol-4yl)-2-(hydroxyimino)acetamido-3-[(Z)-prop-1-en-1-yl]-3-cephem-4-carboxylate,

(33) 7β-[(Z)-2-(2-aminothiazol-4-yl)-2-(hydroxyimino)acetamido]-3-[(E)-prop-1-en-1-yl]-3-cephem-4-carboxylic acid,

(34) acetoxymethyl 7β-[(Z)-2-(2-aminothiazol-4-yl)-2-(hydroxyimino)acetamido]-3-[(E)-prop-1-en-1-yl]-3-cephem-4-carboxylate,

(35) 1-acetoxyethyl 7β-[(Z)-2-(2-aminothiazol-4-yl)-2-(hydroxyimino)acetamido]-3-[(E)-prop-1-en-1-yl]-3-cephem-4-carboxylate,

(36) pivaloyloxymethyl 7β-[(Z)-2-(2-aminothiazol-4-yl)-2-(hydroxyimino)acetamido]-3-[(E)-prop-1-en-1-yl]-3-cephem-4-carboxylate,

(37) 7β-[(Z)-2-(2-aminothiazol-4-yl)-2-(hydroxyimino)acetamido]-3-[(Z)-3-acetoxyprop-1-en-1-yl]-3-cephem-4-carboxylic acid,

(38) acetoxymethyl 7β-[(Z)-2-(2-aminothiazol-4-yl)-2-(hydroxyimino)acetamido]-3-](Z)-3-acetoxyprop-1-en-1-yl]-3-cephem-4-carboxylate,

(39) 1-acetoxyethyl 7β-[(Z)-2-(2-aminothiazol-4-yl)-2-(hydroxyimino)acetamido]-3-[(Z)-3-acetoxyprop-1-en-1-yl]-3-cephem-4-carboxylate,

(40) pivaloyloxymethyl 7β-[(Z)-2-(2-aminothiazol-4-yl)-2-(hydroxyimino)acetamido]-3-[(Z)-3-acetoxyprop-1-en-1-yl]-3-cephem-4-carboxylate,

(41) 7β-[(Z)-2-(2-aminothiazol-4-yl)-2-(hydroxyimino)acetamido]-3-[(E)-3-acetoxyprop-1-en-1-yl]-3-cephem-4-carboxylic acid,

(42) acetoxymethyl 7β-[(Z)-2-(2-aminothiazol-4-yl)-2-(hydroxyimino)acetamido]-3-[(E)-3-acetoxyprop-1-en-1-yl]-3-cephem-4-carboxylate,

(43) 1-acetoxyethyl 7β-[(Z)-2-(2-aminothiazol-4-yl)-2-(hydroxyimino)acetamido]-3-[(E)-3-acetoxyprop-1-en-1-yl]-3-cephem-4-carboxylate,

(44) pivaloyloxmethyl 7β-[(Z)-2-(2-aminothiazol-4-yl)-2-(hydroximino)acetamido]-3-[(E)-acetoxyprop-1-en-1-yl]-3-cephem-4-carboxylate,

(53) 7β-[(Z)-2-(2-aminothiazol-4-yl)-2-(acetoxyimino)acetamido]-3-[(Z)-prop-1-en-1-yl]-3-cephem-4-carboxylic acid,

(54) acetoxymethyl 7β-[(Z)-2-(2-aminothiazol-4-yl)-2-(acetoxyimino)acetamido]-3-[(Z)-prop-1-en-1-yl]-3-cephem-4-carboxylate,

(55) 1-acetoxyethyl 7β-[(Z)-2-(2-aminothiazol-4-yl)-2-(acetoxyimino)acetamido]-3-[(Z)-prop-1-en-1-yl]-3-cephem-4-carboxylate,

(56) pivaloyloxymethyl 7β-[(Z)-2-(2-aminothiazol-4-yl)-2-(acetoxyimino)acetamido]-3-[(Z)-prop-1-en-1-yl]-3-cephem-4-carboxylate,

(57) 5-methyl-2-oxo-1,3-dioxolen-4-ylmethyl 7β-[(Z)-2-(2-aminothiazol-4-yl)-2-(acetoxyimino)acetamido]-3-[(Z)-prop-1-en-1-yl]-3-cephem-4-carboxylate,

(58) 7β-[(Z)-2-(2-aminothiazol-4-yl)-2-(acetoxyimino)acetamido]-3-[(E)-prop-1-en-1-yl]-3-cephem-4-carboxylic acid,

(59) acetoxymethyl 7β-[(Z)-2-(2-aminothiazol-4-yl)-2-(acetoxyimino)acetamido]-3-[(E)-prop-1-en-1-yl]-3-cephem-4-carboxylate,

(60) 1-acetoxyethyl 7β-[(Z)-2-(2-aminothiazol-4-yl)-2-(acetoxyimino)acetamido]-3-[(E)-prop-1-en-1-yl]-3-cephem-4-carboxylate,

(61) pivaloyloxymethyl 7β-[(Z)-2-(2-aminothiazol-4-yl)-2-(acetoxyimino)acetamido]-3-[(E)-prop-1-en-1-yl]-3-cephem-4-carboxylate,

(62) 5-methyl-2-oxo-1,3-dioxolen-4-ylmethyl 7β-[(Z)-2-(2-aminothiazol-4-yl)-2-(acetoxyimino)acetamido]-3-[(E)-prop-1-en-1-yl]-3-cephem-4-carboxylate,

(63) 7β-[(Z)-2-(2-aminothiazol-4-yl)-2-(acetoxyimino)acetamido]-3-[(Z)-3-acetoxyprop-1-en-1-yl]-3-cephem-4-carboxylic acid,

(64) acetoxymethyl 7β-[(Z)-2-(2-aminothiazol-4-yl)-2-(acetoxyimino)acetamido]-3-[(Z)-3-acetoxyprop-1-en-1-yl]-3-cephem-4-carboxylate,

(65) 1-acetoxyethyl 7β-[(Z)-2-(2-aminothiazol-4-yl)-2-(acetoxyimino)acetamido]-3-[(Z)-3-acetoxyprop-1-en-1-yl]-3-cephem-4-carboxylate,

(66) pivaloyloxymethyl 7β-[(Z)-2-(2-aminothiazol-4-yl)-2-(acetoxyimino)acetamido]-3-[(Z)-3-acetoxyprop-1-en-1-yl]-3-cephem-4-carboxylate,

(67) 5-methyl-2-oxo-1,3-dioxolen-4-ylmethyl 7β-[(Z)-2-(2-aminothiazol-4-yl)-2-(acetoxyimino)acetamido]-3-[Z]-3-acetoxyprop-1-en-1-yl]-3-cephem-4-carboxylate.

(68) 7β-[(Z)-2-(2-aminothiazol-4-yl)-2-(acetoxyimino)acetamido]-3-[(E)-3-acetoxyprop-1-en-1-yl]-3-cephem-4-carboxylic acid,

(69) acetoxymethyl 7β-[(Z)-2-(2-aminothiazol-4-yl)-2-(acetoxyimino)acetamido]-3-[(E)-3-acetoxyprop-1-en-1-yl]-3-cephem-4-carboxylate,

(70) 1-acetoxyethyl 7β-[(Z)-2-(2-aminothiazol-4-yl)-2-(acetoxyimino)acetamido]-3-[(E)-3-acetoxyprop-1-en-1-yl]-3-cephem-4-carboxylate,

(71) pivaloyloxymethyl 7β-[(Z)-2-(2-aminothiazol-4-yl)-2-(acetoxyimino)acetamido]-3-[(E)-3-acetoxyprop-1-en-1-yl]-3-cephem-4-carboxylate,

(72) 5-methyl-2-oxo-1,3-dioxolen-4-ylmethyl 7β-[(Z)-2-(2-aminothiazol-4-yl)-2-(acetoxyimino)acetamido]-3-[(E)-3-acetoxyprop-1-en-1-yl]-3-cephem-4-carboxylate,

(88) (5-methyl-2-oxo-1,3-dioxolen-4-yl)methyl 7β-[(Z)-2-(2-aminothiazol-4-yl)-2-(hydroxyimino)-acetamido]-3-[(Z)-prop-1-en-1-yl]-3-cephem-4-carboxylate.

(89) 1-(ethoxycarbonyloxy)ethyl 7β-[(Z)-2-(2-aminothiazol-4-yl)-2-(hydroxyimino)-acetamido]-3-[(Z)-prop-1-en-1-yl]-3-cephem-4-carboxylate.

(90) 1-(cyclohexyloxycarbonyloxy)ethyl 7-[(Z)-2-(2-aminothiazol-4-yl)-2-(hydroxyimino)acetamido]-3-[(Z)-1-propenyl]-3-cephem-4-carboxylate.

(91) 1-(pivaloyloxy)ethyl 7-[(Z)-2-(2-aminothiazol-4-yl)-2-(hydroxyimino)acetamido]-3-[(Z)-1-propenyl]-3-cephem-4-carboxylate.

(92) 1-(cyclohexylacetoxy)ethyl 7-[(Z)-2-(2-aminothiazol-4-yl)-2-(hydroxyimino)acetamido]-3-[(Z)-1-propenyl]-3-cephem-4-carboxylate.

The in vitro antibacterial activity of the parent cephalosporanic acids of Formula I wherein $R^4$ is hydrogen is shown in Table 1 in terms of geometric mean of the Minimum Inhibitory Concentrations (MIC's) which were determined by the two-fold serial agar dilution method in Mueller-Hinton agar against 25 strains of test organisms in five groups.

Table 2 shows the mouse blood levels of pro-drug esters of Formula I which were determined after oral administration.

Table 3 shows the structures of pro-drug esters Nos. 88–92.

Tables 4 and 5 show the in vivo activity of pro-drug esters 88–92 including the bioavailability thereof as reflected by blood levels.

Table 6 is a comparison of the in vitro antibacterial activities of Compound 29 and the vinyl homolog thereof FK-482 against clinically important pathogens. Thirty-seven organisms were more than 4-fold more susceptible to Compound 29 than to FK-482. FK-482 has the following formula and is described by Takaya, et al. in U.S. Pat. No. 4,559,334 patented Dec. 17, 1985 (filed Oct. 20, 1983).

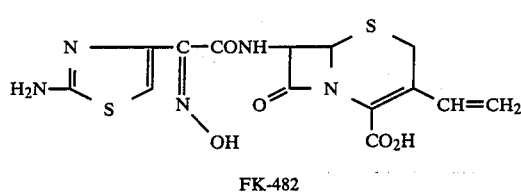

FK-482

TABLE 1

In vitro Activity of Cephalosporin Acids (Ia)

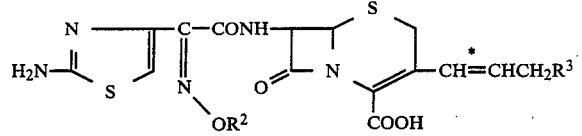

| | Ia | | | Geometric mean of MIC (mcg/ml) | | | | |
|---|---|---|---|---|---|---|---|---|
| Compound No. (BMY No.) | * | $R^2$ | $R^3$ | GpIa (5*) | GpIb (5) | GnIa (5) | GnIb (5) | GnII (5) |
| 29 (28232) | Z | H | H | 0.20 | 0.40 | 0.066 | 0.35 | 6.3 |
| 33 (28286) | E | H | H | 0.23 | 0.61 | 0.46 | 1.4 | 22 |
| 37 (28266) | Z | H | OAc | 0.17 | 0.40 | 0.025 | 0.1 | 1.1 |
| 53 (28270) | Z | Ac | H | 0.17 | 0.40 | 0.057 | 0.26 | 3.6 |
| Cefadroxil | | | | 1.4 | 3.6 | 8.3 | 17 | >100 |
| Cefaclor | | | | 0.7 | 4.7 | 0.92 | 11 | >100 |
| Cefixime[1] (FK-027) | | | | 4.7 | 12.5 | 0.016 | 3.1 | 3.2 |

Gp-Ia: Penicillin(PC)-sensitive *S. aureus*
Gp-Ib: PC-resistant *S. aureus*
Gn-Ia: Cephalothin(CET)-sensitive *E. coli* (2 strains), *K. pneumoniae* (1) and *P. mirabilis* (2)
Gn-Ib: CET-resistant *E. coli* (3) and *K. pneumoniae* (2)
Gn-II: *M. morcanii* (1), *E. cloacae* (2) and *S. marcescens* (2)

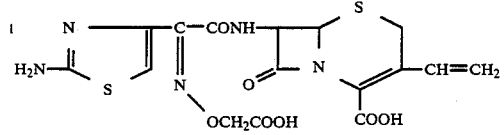

TABLE 2

Mouse Blood Levels of Pro-Drug Esters (Ib)

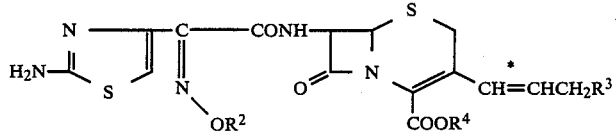

| | Ib | | | | 100 mg/kg, po | | | 20 mg/kg, po | | |
|---|---|---|---|---|---|---|---|---|---|---|
| Compound No. (BMY No.) | $R^2$ | $R^3$ | $R^4$ | * | $C_{max}$ (mcg/ml) | T½ (hr) | AUC (mcg hr/ml) | $C_{max}$ (mcg/ml) | T½ (hr) | AUC (mcg hr/ml) |
| 30 (28271) | H | H | AX[3] | Z | 36 | 1.3 | 61 | 9.9 | 1.0 | 16 |
| 39 (28277) | H | OAc | AX | Z | | | | | | |
| 55 (28258) | Ac | H | AX | Z | 27 | 0.8 | 40 | 7.6 | 0.8 | 9.4 |
| Cefaclor | | | | | 26 | 1.2 | 35 | 8.5 | 0.91 | 8.9 |
| Cefixime | | | | | 28 | 1.6 | 75 | 10 | 1.5 | 25 |
| Cefadroxil | | | | | 57 | 1.6 | 69 | 12 | 1.4 | 16 |

[3]AX = —CH(CH₃)OCOCH₃

TABLE 3

Additional Physiologically Hydrolyzable Esters

| Compound No. (BMY No.) | $R^2$ | $R^3$ | $R^4$ |
|---|---|---|---|
| 88 (28352) | H | KB | CH₃(Z) |
| 89 (28353) | H | BC | CH₃(Z) |
| 90 (28632) | H | CC | CH₃(Z) |
| 91 (28633) | H | PE | CH₃(Z) |
| 92 (28644) | H | CX | CH₃(Z) |

BC 1-(ethoxycarbonyloxy)ethyl
KB (5-methyl-2-oxo-1,3-dioxolen-4-yl)methyl
CC 1-(cyclohexyloxycarbonyloxy)ethyl
PE 1-(pivaloyloxy)ethyl
CX 1-(cyclohexylacetoxy)ethyl

TABLE 4

Evaluation In Vivo (mouse) of BC and KB Esters

| Compound No. (BMY No) | Ester Type | Oral $PD_{50}$ (mg/kg) S. aureus Smith | Oral $PD_{50}$ (mg/kg) E. coli Juhl | Blood Concentration* $C_{max}$ (mcg/ml) | Blood Concentration* AUC (mcg.hr/ml) |
|---|---|---|---|---|---|
| 89 (28353) | BC | 0.77 | 0.67 | 32 | 74 |
| 88 (28352) | KB | 1.1 | 2.7 | 16 | 44 |

*treated orally, single 100 mg/kg. dose

TABLE 5

Evaluation In Vivo (mouse) Additional Physiologically Hydrolyzable Esters

| Compound No. (BMY No.) | Ester Type | Oral $PD_{50}$ (mg/kg) S. aureus Smith | Oral $PD_{50}$ (mg/kg) E. coli Juhl | Bio-availability (%)* |
|---|---|---|---|---|
| 30 (28271) | AX | 2.0 | 1.1 | 76 |
| 90 (28632) | CC | 3.2 | 1.5 | 78 |
| 91 (28633) | PE | 2.0 | 3.5 | 60 |
| 92 (28644) | CX | 2.9 | 1.4 | 87 |

*Bioavailability = $\frac{\text{AUC of test compound (po, 100 mg/kg)}}{\text{AUC of Compound No. 29(IV, 100 mg/kg)}}$

TABLE 6

In Vitro Antibacterial Activity of Compound 29 and FK-482

| Test organism | | MIC (μg/ml) Compound 29 | MIC (μg/ml) FK-482 |
|---|---|---|---|
| Citrobacter freundii | A21312 | >50 | >50 |
| " | A22140 | 1.6 | 3.1 |
| " | A22141 | 1.6 | 3.1 |
| " | A22142 | 0.8 | 0.8 |
| " | A22160 | 0.8 | 6.3 |
| " | A22161 | 0.8 | 0.8 |
| " | A22166 | 0.8 | 3.1 |
| " | A22175 | 0.8 | 0.8 |
| " | A22176 | 0.8 | 3.1 |
| " | A22177 | 3.1 | 50 |
| | (GM)* | 1.7 | 4.1 |
| Enterobacter cloacae | A20650 | 0.8 | 0.8 |
| " | A 9659 | >50 | >50 |
| " | A 9655 | 50 | >50 |
| " | A20364 | 3.1 | 6.3 |
| " | A20344 | >50 | >50 |
| " | A20464 | 3.1 | 3.1 |
| " | A22551 | >50 | >50 |
| | (GM) | 17 | 21 |
| Enterobacter aerogenes | A20940 | >50 | >50 |
| " | A20941 | 1.6 | 6.3 |
| " | A20943 | 0.8 | 6.3 |
| " | A20958 | 6.3 | 6.3 |
| " | A20961 | 3.1 | 12.5 |
| " | A20966 | 6.3 | 6.3 |
| " | A20971 | 1.6 | 6.3 |
| " | A20985 | >50 | >50 |
| " | A20994 | 6.3 | 25 |
| " | A20996 | 0.8 | 3.1 |
| " | A21013 | 3.1 | 6.3 |
| " | A21036 | >50 | 50 |
| " | A21037 | 0.4 | 3.1 |
| " | A21038 | 0.8 | 1.6 |
| " | A21039 | 6.3 | 6.3 |
| " | A21043 | 12.5 | 25 |
| " | A21044 | 25 | 25 |
| " | A21118 | 50 | >50 |
| " | A21120 | 6.3 | 6.3 |
| " | A21130-1 | 6.3 | 6.3 |
| " | A21131 | 0.8 | 6.3 |
| " | A21152 | 0.8 | 1.6 |
| " | A21155 | 3.1 | 6.3 |
| " | A21158 | 6.3 | 6.3 |
| " | A21503 | 3.1 | 6.3 |
| | (GM) | 4.9 | 9.8 |
| Morganella morganii | A 9636 | >50 | >50 |
| " | A20455 | 1.6 | 12.5 |
| " | IFO 3843 MS-1 | 1.6 | 12.5 |
| | (GM) | 6.3 | 25 |

TABLE 6-continued

In Vitro Antibacterial Activity of Compound 29 and FK-482

| Test organism | | MIC (μg/ml) Compound 29 | MIC (μg/ml) FK-482 |
|---|---|---|---|
| Proteus mirabilis | A20119 | 0.05 | 0.1 |
| " | A20454 | 0.1 | 0.1 |
| " | A 9702 | 0.05 | 0.1 |
| " | A21222 | 0.1 | 0.1 |
| " | A20342 | 0.1 | 0.2 |
| " | A 9716 | 0.1 | 0.2 |
| " | A 9554 | 0.1 | 0.2 |
| " | IFO 3849 MS-1 | 0.1 | 0.2 |
| | (GM) | 0.084 | 0.14 |
| Proteus vulgaris | A 9436 | 0.1 | 0.4 |
| " | A 9526 | 3.1 | 25 |
| " | A 9699 | 1.6 | 25 |
| " | AKH-26 | >50 | >50 |
| " | OX-19 MS-1 | 0.2 | 3.1 |
| " | HX-19 MS-1 | 0.1 | 0.8 |
| | (GM) | 1.0 | 6.3 |
| Providencia rettgeri | A15167 | <0.0063 | 0.013 |
| " | A 9637 | <0.0063 | <0.0063 |
| " | A15167 | 0.013 | 0.1 |
| " | A20645 | 0.4 | 6.3 |
| " | A20915 | 0.8 | 3.1 |
| " | A20920 | <0.0063 | 0.013 |
| " | A20921 | <0.0063 | 0.025 |
| " | A21270 | 0.025 | 0.1 |
| " | A21205 | 0.025 | 0.1 |
| " | IFO 3850 MS-1 | <0.0063 | 0.013 |
| | (GM) | 0.015 | 0.070 |
| Serratia marcescens | A20019 | 1.6 | 12.5 |
| " | A20335 | 1.6 | 12.5 |
| " | A20336 | 3.1 | 12.5 |
| " | A20442 | 3.1 | 3.1 |
| " | A20222 | 3.1 | 25 |
| " | A20460 | 12.5 | 50 |
| " | A20333 | >50 | >50 |
| " | A20334 | >50 | >50 |
| " | A20459 | >50 | >50 |
| " | A20461 | >50 | >50 |
| | (GM) | 13 | 31 |
| Serratia species | 9-50 | >50 | >50 |
| " | 9-690 | >50 | >50 |
| " | 8-1537 | 25 | >50 |
| " | 8-185 | >50 | >50 |
| " | 8-513 | 25 | >50 |
| " | 8-785 | >50 | >50 |
| " | 7-2322 | >50 | >50 |
| " | 7-255 | >50 | >50 |
| " | 7-454 | >50 | >50 |
| " | 6-427 | 3.1 | 25 |
| " | 6-920 | >50 | >50 |
| " | 6-330 | 3.1 | 25 |
| | (GM) | 44 | >50 |

*; Geometric mean of MIC (μg/ml)
Mueller-Hinton agar Inoculum size; $10^6$ cells/ml
In the following examples the abreviations used have their conventional meanings including the following.
DMF dimethylformamide
TFA trifluoroacetic acid
Tr trityl or triphenylmethyl
THF tetrahydrofuran
DCC dicyclohexylcarbodiimide The esters are prepared in the following examples by reacting the acid, Formula I wherein $R^4$ is hydrogen, or a salt thereof, (sodium, potassium, triethylammonium, etc.) with a halogenated compound of the formula $R^4$—X wherein X is chloro, bromo, or iodo and $R^4$ is a group selected from —$CH_2OCOC(CH_3)_3$, —CHOCOCH$_3$,
$\phantom{CCCCCCCCCCCCCCCCCCCCCCCC}$ |
$\phantom{CCCCCCCCCCCCCCCCCCCCCCCC}$ $CH_3$ -continued

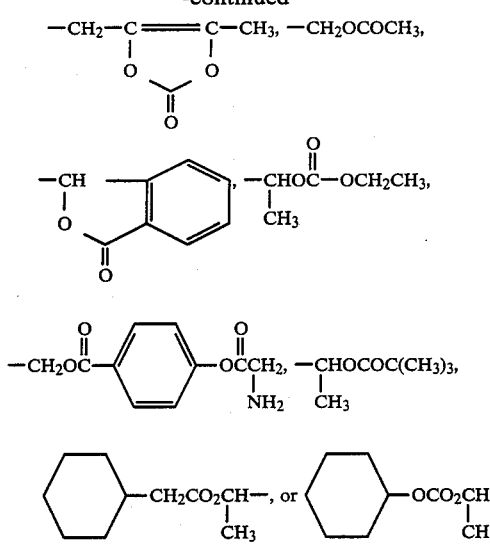

The reaction is carried out effectively in an inert organic solvent such as N,N-dimethylformamide, N,N-dimethylacetamide, dimethylsulfoxide, acetone, acetonitrile, or the like, at a temperature in the range of from −10° C. to +50° C., conveniently between 0° C. and 5° C. The ester thus obtained is purified by conventional column chromatograph by using silica gel. Other methods may also be employed.

EXAMPLE 1

Diphenylmethyl 7-Amino-3-(1-propenyl)-3-cephem-4-carboxylate

To a solution of diphenylmethyl 7-benzylideneamino-3-[(triphenylphosphoranylidene)methyl]-3-cephem-4-carboxylate (2.9 g, 4 mmoles) in dichloromethane (16 ml) was added 90% acetaldehyde (10 ml, 0.2 mole). The mixture was stirred at room temperature for 30 minutes, dried over sodium sulfate and concentrated in vacuo. The residue was dissolved in ethyl acetate (80 ml). To the solution was added isopropyl ether (160 ml) and then silica gel (25 g). The mixture was gently agitated and filtered to remove the solid. The filtrate was evaporated into dryness in vacuo. To a solution of the residue in ethyl acetate (48 ml) was added a mixture of Girard's reagent T (1.34 g, 8 mmoles), methanol (40 ml) and acetic acid (2 ml). The mixture was stirred at room temperature for 30 minutes and concentrated to ca. 10 ml. The residue was dissolved in ethyl acetate (100 ml). The solution was washed with aqueous sodium bicarbonate and water, dried over sodium sulfate and concentrated in vacuo. The residue was chromatographed on a silica gel column (50 g), which was eluted with 1% methanol in chloroform. The eluate was collected in 18-ml fractions. Fraction Nos. 22–40 were combined and concentrated to give 718 mg of the 3-propenyl derivative (Yield 44%, E/Z=⅓).

TLC: Rf 0.56 (silica gel, ethyl acetate).

HPLC*: Retention time (min.) 13.2 and 15.6 (relative intensity=3:1).

IR: $\nu_{max}$ (KBr) in cm$^{-1}$ 1770, 1720.

UV: $\lambda_{max}$ (C$_2$H$_5$OH) in nm ($\epsilon$) 214 (20500), 222 (20800), 266 (4200), 273 (4200), 292 (3800).

NMR (a 1:3 mixture of E and Z isomers): δ (CDCl$_3$) in ppm 1.42 and 1.72 (relative intensity=3:1) (both are dd, J=2 and 7 Hz, CH$_3$).

EXAMPLE 33

Diphenylmethyl 7-[(Z)-2-(2-Tritylaminothiazol-4-yl)-2-trityloxyiminoacetamido]-3-((Z)-1-propenyl)-3-cephem-4-carboxylate To a mixture of 2-(2-tritylaminothiazol-4-yl)-2-(Z)-trityloxyiminoacetic acid (873 mg, 1.30 m moles) and dichloromethane (5 ml) was added phsophorous pentachloride (297 ng, 1.43 m moles) at −5° C. The mixture was allowed to stand for 20 min at the same temperature and added dropwise to a solution of diphenylmethyl 7-amino-3-(1-propenyl)-3-cephem-4-carboxylate hydrochloride (443 mg, 1 m mole) and N,O-bis(trimethylsilyl)acetamide (0.74 ml, 4.4 m moles) in dichloromethane (5 ml) at −5° C. The reaction mixture was allowed to stand for 20 min. at the same temperature and poured into ice-water. Extraction of the mixture with ethyl acetate and evaporation of the extracts under reduced pressure gave the crude product as an oil, which was chromatographed on a column of silica gel (eluted with chloroform) to give the title compound as an amorphous powder. Yield 510 mg (48%).

IR: $\nu_{max}$ (nujol) in cm$^{-1}$ 1780, 1720, 1680.

*R. Bucourt et al., Tetrahedron 34, 2233 (1978)

EXAMPLE 34

7-[(Z)-2-(2-Aminothiazol-4-yl)-2-hydroxyiminoacetamido)-3-[(Z)-1-propenyl-3-cephem-4-carboxylic Acid A mixture of the product of Example 33 (810 mg, 0.76 m mole) and 85% formic acid (2 ml) was stirred for 1 hr at room temperature. To the reaction mixture was added hydrochloric acid (0.1 ml). The mixture being stirred for 2 hr and evaporated under reduced pressure, the residue was triturated with isopropyl ether to give the crude product, which was chromatographed on a column of C-18 silica gel (eluted with 20% aq. MeOH). The eluate was concentrated under reduced pressure and freeze-dried to give the title compound as an amorphous powder. Yield 109 mg (35%). M.p. 170° C. (dec.). Est'd purity 75%.

IR: $\nu_{max}$ (KBr) in cm$^{-1}$ 1770, 1760, 1630.

UV: $\lambda_{max}$ (pH 7 phosphate buffer) in nm (E$_{1\ cm}$1%) 225 (450), 282 (370).

NMR: δ (D$_2$O+NaHCO$_3$) in ppm 1.78 (3H, d, J=6 Hz, CH=CH—CH$_3$), 3.64 (2H, ABq, J=18 Hz, 2-H), 5.40 (1H, d, J=4 Hz, 6-H), 5.70–6.25 (3H, m, 7-H, vinyl-H), 7.14 (1H, d, thiazole-H).

EXAMPLE 45

7-Amino-3-[(E)-1-propenyl]-3-cephem-4-carboxylic Acid

A solution of 7-amino-3-[(Z)-1-propenyl]-3-cephem-4-carboxylic acid* (1.2 g, 5 m moles) and benzophenone (900 mg, 5 m moles) in methanol (800 ml) containing 1 ml of 6N hydrochloric acid was irradiated with low-pressure Hg lamp (2537 Å, 6 W) at room temperature for 44 hrs. The reaction mixture was evaporated to dryness and the residue was distributed in a mixture of 0.15N HCl (200 ml) and ether (200 ml). The aqueous layer was separated, treated with active carbon and filtered. The filtrate was adjusted to pH 3 with a dilute NaOH solution and cooled to give a precipitate. It was collected by filtration and washed with water and acetone to give 476 mg of the title compound E isomer, melting at 245° C. (grad. dec.). The second crop (195 mg) was obtained by concentrating the filtrate to 30 ml. Total yield 671 mg (56%). The product contained less than 5% of the corresponding Z isomer.

IR: $\nu_{max}$ (KBr) in cm$^{-1}$ 1800, 1620, 1540, 1420, 1360.

UV: $\lambda_{max}$ (pH 7 phosphate buffer) in nm ($\epsilon$) 292 (15000).

NMR: $\delta$ (D$_2$O+Na$_2$CO$_3$) in ppm 1.78 (3H, d, J=6 Hz, =CH—CH$_3$), 3.62 (2H, s, 2-H), 5.03 (1H, d, J=4.5 Hz, 6-H), 5.3–6.2 (2H, m =CH & 7-H), 6.52 (1H, d, J=16 Hz, 3-CH=C).

Anal. Calcd. for C$_{10}$H$_{12}$N$_2$O$_3$S.$\frac{1}{2}$H$_2$O: C, 47.18; H, 5.25; N, 11.24; S, 12.86. Found: C, 47.88; H, 4.83; N, 10.79; S, 12.83.

A 4:1 mixture of Z and E isomers.

COMPOUND 33, EXAMPLE 63

7-[(Z)-2-(2-Aminothiazol-4-yl)-2-hydroxyiminoacetamido]-3-[(E)-1-propenyl]-3-cephem-4-carboxylic Acid A mixture of the crude product of Example 33 containing 20% of its E isomer (9.2 g, 8.7 mmol) in 85% HCOOH (60 ml) was stirred for 1 hr at room temperature and evaporated in vacuo. The residue was treated with 90%-TFA (60 ml) for 1 hr at room temperature and poured into ice-water (300 ml). The insolubles were filtered off. The filtrate was chromatographed on a reverse phase column (Waters, prepPAK C18, 300 ml) and the column was eluted with 20% MeOH. The polar fractions were combined, concentrated in vacuo and the residue was triturated with isopropyl ether to give 1.15 g (33%) of the Z isomer and the less polar fractions gave 143 mg (4%) of the title compound.

mp >200° C. (dec). IR $\nu_{max}$ (KBr) cm$^{-1}$ 1760, 1660, 1630, 1530. UV $\lambda_{max}$ (pH 7 phosphate buffer) nm ($\epsilon$) 223 (20000), 290 (21000). $^1$H NMR (D$_2$O) $\delta$ 1.38 (3H, d, J=7.0 Hz), 3.73 (2H, br.s), 5.30 (1H, br.s), 5.85 (1H, d, J=5.0 Hz), 5.80–6.30 (1H, m), 6.57 (1H, d, J=16 Hz), 7.06 (1H, s).

Anal Calcd for C$_{15}$H$_{15}$N$_5$O$_5$S$_2$.1.5H$_2$O: C 41.28, H, 4.16, N 16.05, S 14.65. Found: C 41.46, H, 3.60, N 15.86, S 14.83.

COMPOUND 40, EXAMPLE 64

Pivaloyloxymethyl 7-[(Z)-2-(2-Aminothiazol-4-yl)-2-hydroxyiminoacetamido]-3-[(Z)-3-acetoxy-1-propenyl]-3-cephem-4-carboxylate To an ice-cooled mixture of Compound No. 37 (170 mg, 0.36 mmol) and Na$_2$CO$_3$ (20 mg, 0.19 mmol) in dry DMF (2 ml) was added pivaloyloxymethyl iodide (87 mg, 0.36 mmol) and the mixture was stirred for 10 min at the same temperature. Additional amount of pivaloyloxymethyl iodide (87 mg) and Na$_2$CO$_3$ (20 mg) was added and the mixture was stirred for additional 10 min. The mixture was diluted with ethyl acetate, washed with water and evaporated under reduced pressure. Chromatography of the residue on a silica gel column and elution with CHCl$_3$-MeOH (1–2%) gave the product as an amorphous powder. Yield 110 mg (52%). mp 95°–100° C. (dec.). IR $\nu_{max}$ (KBr) cm$^{-1}$ 1780, 1740, 1670, 1530. UV $\lambda_{max}$ (EtOH) nm ($\epsilon$) 280 (11400). $^1$H NMR (CDCl$_3$) $\delta$ 1.20 (9H, s, t-Bu), 2.0 (3H, s, OAc), 3.45 (2H, s, 2-H), 4.50 (2H, d, J=7 Hz, CH$_2$OAc), 5.10 (1H, d, J=5 Hz, 6-H), 5.3–6.0 (4H, m, 7-H, vinyl-H, CH$_2$OCO), 6.25 (1H, d, J=12 Hz, vinyl-H), 7.0 (1H, s, thiazole-H), 11.5 (1H, d, J=8 Hz, CONH).

COMPOUND 41, EXAMPLE 65

7-[(Z)-2-(2-Aminothiazol-4-yl)-2-hydroxyiminoacetamido]-3-[(E)-3-acetoxy-1-propenyl]-3-cephem-4-carboxylic Acid (a) Acylation To a solution of 1-hydroxybenzotriazole (223 mg, 1.44 mmol) and (Z)-2-(2-tritylaminothiazol-4-yl)-2-trityloxyiminoacetic acid (1.06 g, 1.44 mmol) in THF (14 ml) was added DCC (300 mg, 1.44 mmol) and the mixture was stirred for 1 hr at 5° C. Diphenylmethyl 7-amino-3-[(E)-acetoxy-1-propenyl]-3-cephem-4-carboxylate (670 mg, 1.44 mmol) was added to the mixture. After stirring for 4 hr at ambient temperature, the reaction mixture was filtered, diluted with ethyl acetate (50 ml) and washed with water. Concentration of the organic layer gave an oil, which was chromatographed on a column of silica gel. Elution with toluene-ethyl acetate (10:1) gave 1.607 g (99%) of diphenylmethyl 7-[(Z)-2-(2-tritylaminothiazol-4-yl)-2-trityloxyiminoacetamido]-3-[(E)-3-acetoxy-1-propenyl]-3-cephem-4-carboxylate as an amorphous powder. IR $\nu_{max}$ (KBr) cm$^{-1}$ 1770, 1730. $^1$H NMR (CDCl$_3$) $\delta$ 2.0 (3H, s, OAc), 3.33 (2H, s, 2-H), 4.54 (2H, ABq, CH$_2$OAc), 5.04 (1H, d, J=5 Hz, 6-H), 6.0 (1H, m, vinyl-H), 6.02 (1H, dd, J=5 & 7 Hz, 7-H), 6.40 (1H, s, thiazole-H), 6.82 (1H, d, J=15 Hz, vinyl-H), 7.00 (1H, s, Ph$_2$CH), 7.3 (25H, s, Ph).

(b) Deblocking

A mixture of diphenylmethyl 7-[(Z)-2-(2-tritylaminothiazol-4-yl)-2-trityloxyiminoacetamido]-3-[(E)-3-acetoxy-1-propenyl]-3-cephem-4-carboxylate (1.98 g, 1.75 mmol) in formic acid (20 ml) was stirred for 2 hr at room temperature. Conc. hydrochloric acid (0.16 ml, 1.92 mmol) was added to the mixture and the mixture was stirred for 1 hr at room temperature. Filtration, and concentration of the filtrate, followed by trituration with IPE gave 975 mg of the crude product. Chromatography on a column of reversed phase silica gel and elution with 10% MeOH in water and concentration of the fraction containing the desired product gave 418 mg (51%) of the title compound as an amorphous powder. IR $\nu_{max}$ (KBr) cm$^{-1}$ 1765, 1730, 1650. UV $\lambda_{max}$ (pH 7 phosphate buffer) nm ($\epsilon$) 290 (23400). $^1$H NMR (DMSO-d$_6$) $\delta$ 2.03 (3H, s, OAC), 3.65 (2H, ABq, 2-H), 4.61 (2H, ABq, CH$_2$OAc), 5.15 (1H, d, J=5 Hz, 6-H), 5.75 (1H, dd, J=5 & 8 Hz, 7-H), 6.15 (1H, m, vinyl-H), 6.65 (1H, s, thiazole), 6.85 (1H, d, J=15 Hz, vinyl-H), 7.05 (2H, s, NH$_2$).

COMPOUND 44, EXAMPLE 66

Pivaloyloxymethyl 7-[(Z)-2-(2-Aminothiazol-4-yl)-2-hydroxyiminoacetamido]-3-[(E)-3-acetoxy-1-propenyl]-3-cephem-4-carboxylate To a cooled and stirred mixture of the product of Example 65 (200 mg, 0.43 mmol) and Na$_2$CO$_3$ (22.7 mg, 0.22 mmol) in DMF (2 ml) was added pivaloyloxymethyl iodide (91 mg, 0.43 mmol) and the mixture was stirred at 5° C. for 30 min. The reaction mixture was diluted with ethyl acetate (40 ml), washed with water and brine successively. The organic layer was dried over MgSO$_4$ and concentrated under diminished pressure. The crude product was chromatographed on a column of silica gel. Elution with CHCl$_3$-MeOH (1-3%) gave 123 mg (50%) of the product as an amorphous powder. IR $\nu_{max}$ (KBr) cm$^{-1}$ 3300, 2970, 1780, 1740. UV $\lambda_{max}$ (MeOH) nm ($\epsilon$) 296 (18500). $^1$H NMR (DMSO-d$_6$) δ 1.22 (9H, s, t-Bu), 2.08 (3H, s, OAc), 3.60 (2H, s, 2-H), 4.66 (2H, ABq, CH$_2$OAc), 5.06 (1H, d, J=5 Hz, 6-H), 5.85 (1H, dd, J=5 & 7 Hz, 7-H), 5.88 (2H, ABq, 4-CO$_2$CH$_2$), 6.0 (1H, m, vinyl-H), 7.00 (1H, s, thiazole), 7.1 (1H, d, J=15 Hz, vinyl-H).

COMPOUND 63, EXAMPLE 68

7-[(Z)-2-(2-Aminothiazol-4-yl)-2-acetoxyiminoacetamido]-3-[(Z)-3-acetoxy-1-propenyl]-3-cephem-4-carboxylic Acid (a) Acylation To a mixture of (Z)-2-(tritylaminothiazol-4-yl)-2-acetoxyiminoacetic acid (1.95 g, 4.0 mmol) and 1-hydroxybenzotriazole (600 mg, 4.0 mmol) in THF (14 ml) was added DCC (824 mg, 4.0 mmol) and the mixture was stirred for 1 hr in an ice bath. Diphenylmethyl 7-amino-3-[(Z)-3-acetoxy-1-propenyl]-3-cephem-4-carboxylate (1.30 g, 2.8 mmol) was added to the suspension and the mixture was stirred for 4 hrs at ambient temperature, filterd, and diluted with AcOEt (60 ml). The organic phase was washed with water, dried over MgSO$_4$, and concentrated under reduced pressure. The residue was chromatographed on a column of silica gel (Wakogel C200, 80 g), which was eluted with toluene-AcOEt (6:1). Fractions which contained the product were combined and concentrated in vacuo to give 2.01 g (77%) of diphenylmethyl 7-[(Z)-2-(tritylaminothiazol-4-yl)-2-acetoxyiminoacetamido]-3-[(Z)-3-acetoxy-1-propenyl)-3-cephem-4-carboxylate.

IR $\nu_{max}$ (KBr) cm$^{-1}$ 1780, 1730. $^1$H NMR (CDCl$_3$) δ 2.0 (3H, s, CH$_3$CO), 2.15 (3H, s, CH$_3$CO), 3.45 (2H, ABq, 2-H), 4.20 (2H, ABq, CH$_2$OAc), 5.12 (1H, d, J=5 Hz, 6-H), 5.70 (1H, m, 3-CH=C$\underline{H}$), 5.90 (1H, dd, J=5 & 7 Hz, 7-H), 6.26 (1H, d, J=12 Hz, 3-C$\underline{H}$=CH), 6.95 (1H, s, thiazole), 7.30 (25H, s, phenyl).

(b) Deblocking

A mixture of diphenylmethyl 7-[(Z)-2-(2-tritylaminothiazol-4-yl)-2-acetoxyiminoacetamido]-3-[(Z)-3-acetoxy-1-propenyl)-3-cephem-4-carboxylate (3.2 g, 3.43 mmol) in TFA (20 ml) and anisole (5 ml) was stirred for 1 hr at 5° C. Removal of the solvent followed by trituration with 100 ml of isopropyl ether gave 1.25 g of TFA salt. The crude product was purified by chromatography using a column of C18 Bondapak, which was eluted with water, 10% MeOH in H$_2$O and 20% MeOH in H$_2$O, successively. Appropriate fractions were combined, concentrated in vacuo and lyophilized to afford 395 mg (23%) of the title compound. IR $\nu_{max}$ (KBr) cm$^{-1}$ 3300, 1770, 1670. UV $\lambda_{max}$ (pH 7 phosphate buffer) nm ($\epsilon$) 228 (20300), 284 (15300). $^1$H NMR (DMSO-d$_6$) δ 2.0 (3H, s, CH$_3$CO), 2.15 (3H, s, CH$_3$CO), 4.51 (2H, ABq, CH$_2$-OAc), 5.22 (1H, d, J=5 Hz, 6-H), 5.60 (1H, m, 3-CH=C$\underline{H}$), 5.80 (1H, dd, J=5 & 7 Hz, 7-H), 6.32 (1H, d, J=12 Hz, 3-C$\underline{H}$=CH), 7.05 (1H, s, thiazole).

COMPOUND 65, EXAMPLE 69

1-Acetoxyethyl 7-[(Z)-2-(2-Aminothiazol-4-yl)-2-acetoxyiminoacetamido]-3-[(Z)-3-acetoxy-1-propenyl]-3-cephem-4-carboxylate To a solution of the product of Example 68 (248 mg, 0.49 mmol) in 25 ml of dry DMF was added Na$_2$CO$_3$ (51 mg, 0.49 mmol) and 1-acetoxyethyl bromide (82 mg, 0.49 mmol) at −10° C. The mixture was stirred at 5° C. for 30 min and 82 mg (0.49 mmol) of 1-acetoxyethyl bromide was added to the suspension. After being stirred for 30 min more, the reaction mixture was diluted with AcOEt (50 ml), washed with water (30 ml×3) and brine, dried over MgSO$_4$ and evaporated under diminished pressure. The crude product was purified by silica gel chromatography eluted with 3% MeOH in chloroform. Removal of the solvent from appropriate eluant followed by freeze-drying gave 157 mg (54%) of the title compound, mp 125° C. (dec). IR $\nu_{max}$ (KBr) cm$^{-1}$ 3430, 3290, 1770, 1680. UV $\lambda_{max}$ (pH 7 phosphate buffer) nm ($\epsilon$) 228 (21900), 287 (12700). $^1$H NMR (DMSO-d$_6$) δ 1.51 (3H, d, J=6 Hz, 4-COOCHCH$_3$), 2.02 (3H, s, AcO), 2.06 (3H, s, AcO), 2.22 (3H, s, AcO), 3.47 (2H, br.s, 2-H), 4.46 (1H, q, J=6 Hz, 4-COOCHCH$_3$), 4.55 (2H, ABq, CH$_2$OAc), 5.12 (1H, d, J=5 Hz, 6-H), 5.70 (1H, m, 3-C$\overline{H}$=CH), 5.95 (1H, dd, J=5 & 7 Hz, 7-H), 6.25 (1H, d, J=12 Hz, 3-C$\underline{H}$=CH), 6.92 (1H, s, thiazole).

COMPOUND 88, EXAMPLE 70

(5-Methyl-2-oxo-1,3-dioxolen-4-yl)-methyl 7-[(Z)-2-(2-Aminothiazol-4-yl)-2-hydroxyiminioacetamido]-3-[(Z)-1-propenyl]-3-cephem-4-carboxylate To an ice-cooled and stirred solution of the product of Example 34 (512 mg, 1.25 mmol) in DMF (2 ml) were added sodium carbonate (238.5 mg, 4.5 mmol) and a solution of 4-bromomethyl-5-methyl-1,3-dioxolen-2-one (869 mg, 4.5 mmol) in DMF (6 ml) in three portions at 15 minute intervals. The mixture was diluted with ethyl acetate (50 ml), washed with water and brine, and dried over MgSO$_4$. The filtrate was concentrated in vacuo. The residue was dissolved in a small amount of chloroform and purified by a silica gel column chromatography. (Kiesel gel 60, 30 g). The desired fractions eluted with a mixture of chloroform and methanol (30:1) were combined, and concentrated in vacuo to give 182 mg (29%) of the desired product. mp 115°–120° C. (dec). IR $\nu_{max}$ (KBr) cm$^{-1}$ 1820, 1770, 1735, 1530, 1210, 1190. UV $\lambda_{max}$ (EtOH) nm ($\epsilon$) 225 (sh19000), 287 (12000). $^1$H NMR (CDCl$_3$+D$_2$O) δ 1.62 (3H, d, J=6.0 Hz), 2.18 (3H, s), 3.45 (2H, br, s), 4.68 (2H, s), 5.10 (1H, d, J=5.5 Hz), 5.50–5.90 (1H, m), 5.85 (1h, d, J=5.5 Hz), 6.12 (1H, d, J=12 Hz), 6.95 (1H, s).

COMPOUND 89, EXAMPLE 71

1-Ethoxycarbonyloxyethyl 7-[(Z)-2-(2-Aminothiazol)-4-yl)-2-hydroxyiminoacetamido]-3-[(Z)-1-propenyl]-3-cephem-4-carboxylate To a stirred solution of the product of Example 34, (256 mg, 0.625 mmol) in DMF (2 ml) were added sodium carbonate (40 mg, 0.625 mmol) and a solution of α-iododiethylcarbonate (183 mg, 0.625 mmol) in DMF (1 ml) at 0°–5° C. After the mixture was stirred for 20 min at 5° C., sodium carbonate (40 mg) and a solution of α-iododiethylcarbonate (183 mg) were added and the mixture was stirred for 40 min. The mixture was diluted with ethyl acetate (50 ml), washed with water (50 ml×2), dried over MgSO$_4$ and filtered. The filtrate was concentrated in vacuo. The residue was dissolved in a small amount of chloroform and purified by a silica gel column (Kiesel gel-60, 20 g). The desired fractions eluted with a mixture of chloroform and methanol (30:1) were combined and concentrated in vacuo to give 56 mg (17%) of the desired product. mp 105°–110° C. IR $\nu_{max}$ (KBr) cm$^{-1}$ 1760, 1525, 1370, 1270. UV $\lambda_{max}$ (EtOH) nm ($\epsilon$) 222 (20000), 286 (11000). $^1$H NMR (CDCl$_3$+D$_2$O) δ 1.33 (3H, t, J=7 Hz), 1.57 (3H, d, J=5 Hz), 1.70 (3H, d, J=7 Hz), 3.45 (2H, br.s), 4.23 (2H, q, J=7 Hz), 5.10 (1H, d, J=5.0 Hz), 5.87 (1H, d, J=5.0 Hz), 5.50–6.00 (1H, m), 6.16 (1H, d, J=12 Hz), 6.92 (1H, q, J=5 Hz), 7.00 (1H, s).

COMPOUND 90, EXAMPLE 72

1-(Cyclohexyloxycarbonyloxy)ethyl 7-[(Z)-2-(2-Aminothiazol-4-yl)-2-(hydroxyimino)acetamido]-3-[(Z)-1-propenyl]-3-cephem-4-carboxylate To a mixture of 7-[(Z)-2-(2-aminothiazol-4-yl)-2-hydroxyiminoacetamido]-3-[(Z)-1-propenyl]-3-cephem-4-carboxylic acid (245 mg. 0.60 mmol), K$_2$CO$_3$ (106 mg, 0.77 mmol) and 18-crown-6 (80 mg) in DMF (2.5 ml) was added 1-iodoethyl cyclohexyl carbonate (447 mg, 1.5 mmol) at 5° C. and the mixture was stirred for 45 min at the same temperature. The mixture was diluted with ethyl acetate, washed with water and evaporated under reduced pressure. The residue was chromatographed on a column of silica gel (10 g) and the column was eluted with chloroform containing 1% methanol. The fractions containing the desired product were combined and evaporated under reduced pressure. The residue was dissolved in a small amount of hexane and freeze-dried to give 96 mg (28%) of the product as an amorphous powder.

M.p. 115°–120° C. (dec.).
IR: $\nu_{max}$ (KBr) in cm$^{-1}$ 1760, 1660.
UV: $\nu_{max}$ (EtOH) in nm ($\epsilon$) 284 (12000).
NMR: δ(CDCl$_3$) in ppm 1.0–2.2 (16H, m, cyclohexyl-H, methyl) 3.42 (2H, s, 2-H), 5.07 (1H, d, J=5 Hz, 6-H) 6.15 (1H, d, J=12 Hz, 3-CH=) 6.85 (1H, m, CHCH$_3$) 7.0 (1H, s, thiazole-H)

COMPOUND 91, EXAMPLE 73

1-(Pivaloyloxy)ethyl 7-[(Z)-2-(2-Aminothiazol-4-yl)-2-(hydroxyimino)acetamido]-3-[(Z)-1-propenyl]-3-cephem-4-carboxylate To a mixture of 7-[(Z)-2-(2-aminothiazol-4-yl)-2-hydroxyiminoacetamido]-3-[(Z)-1-propenyl]-3-cephem-4-carboxylic acid (250 mg, 0.61 mmol), K$_2$CO$_3$ (124 mg, 0.90 mmol) and 18-crown-6 (24 mg) in DMF (2.5 ml) was added 1-pivaloyloxyethyl iodide (461 mg, 1.8 mmol) at 5° C. and the mixture was stirred for 45 min at the same temperature. The mixture was diluted with ethyl acetate, washed with water and evaporated under reduced pressure. The residue was chromatographed on a column of silica gel (10 g) and the column was eluted with chloroform containing 1% methanol. The fractions containing the desired product were combined and evaporated under reduced pressure. The residue was dissolved in a small amount of benzene and freeze-dried to give 72 mg (21%) of the product as an amorphous powder.

M.p. 115°–120° C. (dec.).
IR: $\nu_{max}$ in cm$^{-1}$ 1770, 1750, 1670.
UV: $\lambda_{max}$ (EtOH) in nm ($\epsilon$) 285 (11000).
NMR: δ (CDCl$_3$) in ppm 1.20 (9H, s, t-Bu) 1.4–1.8 (6H m, methyl) 3.45 (2H, s, 2-H) 5.10 (1H, d, J=5 Hz, 6-H) 6.13 (1H, d, J=12 Hz, 3-CH=) 6.6–6.98 (1H, m, CHCH$_3$) 7.00 (1H, S, thiazole-H).

Compound 92, EXAMPLE 74

1-(Cyclohexylacetoxy)ethyl 7-[(Z)-2-(2-Aminothiazol-4-yl)-2-(hydroxyimino)acetamido]-3-[(Z)-1-propenyl]-3-cephem-4-carboxylate (2c)

To a mixture of 7-[(2)-2-(2-aminothiazol-4-yl)-2-hydroxyiminoacetamido]-3-[(Z)-1-propenyl]-3-cephem-4-carboxylate acid (409 mg, 1 mmol), K$_2$CO$_3$ (166 mg, 1.2 mmol) and 18-crown-6 (80 mg) in DMF (4 ml) was added 1-cyclohexylacetoxyethyl iodide (888 mg, 3 mmol) at 5° C. and the mixture was stirred for 45 min at the same temperature. The mixture was diluted with ethyl acetate, washed with water and evaporated under reduced pressure. The residue was chromatographed on a column of silica gel (10 g) and the column was eluted with chloroform containing 1% methanol. The fractions containing the desired product were combined and evaporated under reduced pressure. The residue was dissolved in a small amount of benzene and freeze-dried to give 72 mg (12%) of the product as an amorphous powder.

M.p. 115°–120° C. (dec).
IR: $\nu_{max}$ in cm$^{-1}$ 1760, 1680.
UV: $\lambda_{max}$ (EtOH) in nm ($\epsilon$) 285 (11300).
NMR: δ (CDCl$_3$) 0.8–2.2 (16H, m, cyclohexyl-H) 2.20 (2H, d, J=7 Hz, CH$_2$-cyclohexyl) 5.07 (1H, d, J=5 Hz, 6-H) 6.15 (1H, d, J=12 Hz, 3-CH=) 6.9–7.1 (1H, m, CHCH$_3$) 7.0 (1H, s, thiazol-H).

What is claimed is:

1. A compound of the formula

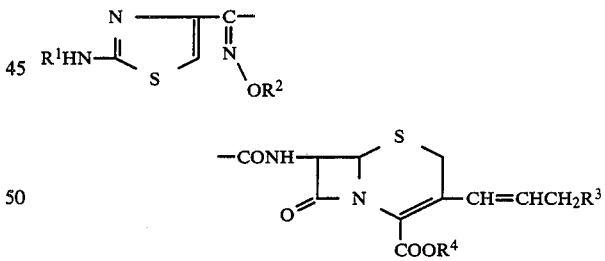

wherein
R$^1$ is hydrogen or a conventional amino-protecting group,
R$^2$ is hydrogen, or alkanoyl having 2 to 4 carbon atoms,
R$^3$ is hydrogen or lower alkanoyloxy having 2 to 3 carbon atoms, and when R$^2$ and R$^3$ are each hydrogen, R$^4$ is also hydrogen, and
R$^4$ is hydrogen, (5-methyl-2-oxo-1,3-dioxolen-4-yl)methyl, 1-(ethoxycarbonyloxy)ethyl, 1-(pivaloyloxy)ethyl, 1-(cyclohexylacetoxy)ethyl, or 1-(cyclohexyloxycarbonyloxy)ethyl.

2. The compound of claim 1 which is 7β-[(Z)-2-(2-aminothiazol-4-yl)-2-(hydroxyimino)acetamido]-3-[(Z)-prop-1-en-1-yl]-3-cephem-4-carboxylic acid.

3. The compound of claim 1 which is 7β-[(Z)-2-(2-aminothiazol-4-yl)-2-(hydroxyimino)acetamido]-3-](E)-prop-1-en-1-yl]-3-cephem-4-carboxylic acid.

4. The compound of claim 1 wherein $R^4$ is (5-methyl-2-oxo-1,3-dioxolen-4-yl)methyl.

5. The compound of claim 4 (5-methyl-2-oxo-1,3-dioxolen-4-yl)methyl 7β-[(Z)-2-(2-aminothiazol-4-yl)-2-(hydroxyimino)acetamido]-3-[(Z)-prop-1-en-1-yl]-3-cephem-4-carboxylate.

6. The compound of claim 1 wherein $R^4$ is 1-(ethoxycarbonyloxy)ethyl.

7. The compound of claim 6, 1-(ethoxycarbonyloxy)ethyl 7β-[(Z)-2-(2-aminothiazol-4-yl)-2-(hydroxyimino)acetamido]-3-[(Z)-prop-1-en-1-yl]-3-cephem-4-carboxylate.

8. The compound of claim 1 where in $R^4$ is 1-(pivaloyloxy)ethyl.

9. The compound of claim 8, 1-(pivaloyloxy)ethyl 7-[(Z)-2-(2-aminothiazol-4-yl)-2-(hydroxyimino)acetamido]-3-[(Z)-1-propenyl]-3-cephem-4-carboxylate.

10. The compound of claim 1 wherein $R^4$ is 1-(cyclohexylacetoxy)ethyl.

11. The compound of claim 10, 1-(cyclohexylacetoxy)ethyl 7-[(Z)-2-(2-aminothiazol-4-yl)-2-(hydroxyimino)acetamido]-3-[(Z)-1-propenyl]-3-cephem-4-carboxylate.

12. The compound of claim 1 wherein $R^4$ is 1-cyclohexyloxycarbonyloxy)ethyl.

13. The compound of claim 12, 1-(cyclohexyloxycarbonyloxy)ethyl 7-[(Z)-2-(2-aminothiazol-4-yl)-2-(hydroxyimino)acetamido]-3-[(Z)-1-propenyl]-3-cephem-4-carboxylate.

* * * * *